United States Patent [19]
Weiss et al.

[11] Patent Number: 5,990,479
[45] Date of Patent: Nov. 23, 1999

[54] ORGANO LUMINESCENT SEMICONDUCTOR NANOCRYSTAL PROBES FOR BIOLOGICAL APPLICATIONS AND PROCESS FOR MAKING AND USING SUCH PROBES

[75] Inventors: Shimon Weiss, Pinole; Marcel Bruchez, Jr., Albany; Paul Alivisatos, Oakland, all of Calif.

[73] Assignee: Regents of the University of California, Oakland, Calif.

[21] Appl. No.: 08/978,450

[22] Filed: Nov. 25, 1997

[51] Int. Cl.$^6$ .............................. G01N 1/30; G01N 21/63
[52] U.S. Cl. ...................... 250/307; 250/459.1; 356/317; 422/82.08; 252/301.17; 378/47; 436/546
[58] Field of Search .................................. 250/307, 302, 250/459.1; 356/317; 252/301.17, 301.33, 301.36; 378/47; 436/172, 546; 422/82.08

[56] References Cited

U.S. PATENT DOCUMENTS

| | | | |
|---|---|---|---|
| 4,637,988 | 1/1987 | Hinshaw et al. | 436/546 |
| 5,262,357 | 11/1993 | Alivisatos et al. | 437/233 |
| 5,319,209 | 6/1994 | Miyakawa et al. | 250/459.1 |
| 5,505,928 | 4/1996 | Alivisatos et al. | 423/299 |
| 5,537,000 | 7/1996 | Alivisatos et al. | 313/506 |
| 5,751,018 | 5/1998 | Alivisatos et al. | 257/64 |

OTHER PUBLICATIONS

Dabbousi, B.O., et al., "(CdSe) ZnS Core–Shell Quantum Dots: Synthesis and Characterization of a Size Series of Highly Luminescent Nanocrystal–lites". *Journal of Physical Chemistry B*, vol. 101, 1997, pp. 9463–9475.

Peng, Xiaogang, et al., "Epitaxial Growth of Highly Luminescent CdSe/Cds Core/Shell Nanocrystals with Photostavility and Electronic Accessibility", *Journal of the American Chemical Society*, vol. 119, No. 30, pp. 7019–7029.

*Primary Examiner*—Jack I. Berman
*Attorney, Agent, or Firm*—John P. Taylor; Paul R. Martin; Kerry S. Taylor

[57] ABSTRACT

A luminescent semiconductor nanocrystal compound is described which is capable of linking to an affinity molecule. The compound comprises (1) a semiconductor nanocrystal capable of emitting electromagnetic radiation (luminescing) in a narrow wavelength band and/or absorbing energy, and/or scattering or diffracting electromagnetic radiation—when excited by an electromagnetic radiation source (of narrow or broad bandwidth) or a particle beam; and (2) at least one linking agent, having a first portion linked to the semiconductor nanocrystal and a second portion capable of linking to an affinity molecule. The luminescent semiconductor nanocrystal compound is linked to an affinity molecule to form an organo luminescent semiconductor nanocrystal probe capable of bonding with a detectable substance in a material being analyzed, and capable of emitting electromagnetic radiation in a narrow wavelength band and/or absorbing, scattering, or diffracting energy when excited by an electromagnetic radiation source (of narrow or broad bandwidth) or a particle beam. The probe is stable to repeated exposure to light in the presence of oxygen and/or other radicals.

Further described is a process for making the luminescent semiconductor nanocrystal compound and for making the organo luminescent semiconductor nanocrystal probe comprising the luminescent semiconductor nanocrystal compound linked to an affinity molecule capable of bonding to a detectable substance. A process is also described for using the probe to determine the presence of a detectable substance in a material.

50 Claims, 3 Drawing Sheets

LINKING TOGETHER A SEMICONDUCTOR NANOCRYSTAL CAPABLE OF EMITTING RADIATION IN A NARROW WAVELENGTH BAND AND ONE OR MORE LINKING AGENTS CAPABLE OF ALSO LINKING TO AN ORGANIC AFFINITY MOLECULE;

AND LINKING TOGETHER AN ORGANIC AFFINITY MOLECULE CAPABLE OF SELECTIVELY BONDING WITH A DETECTABLE SUBSTANCE AND THE ONE OR MORE LINKING AGENTS CAPABLE OF ALSO LINKING TO A SEMICONDUCTOR NANOCRYSTAL;

TO THEREBY FORM AN ORGANO LUMINESCENT SEMICONDUCTOR NANOCRYSTAL PROBE CAPABLE OF BONDING TO A DETECTABLE SUBSTANCE IN A MATERIAL AND, FOR EXAMPLE, TO EMIT RADIATION OF A NARROW WAVELENGTH BAND WHEN EXPOSED TO EXCITATION ENERGY TO INDICATE THE PRESENCE OF THE DETECTABLE SUBSTANCE

FIG. 4

DETERMINING THE PRESENCE OF A DETECTABLE SUBSTANCE IN A BIOLOGICAL MATERIAL BY CONTACTING THE BIOLOGICAL MATERIAL WITH AN ORGANO LUMINESCENT SEMICONDUCTOR NANOCRYSTAL PROBE COMPRISING:

1. A SEMICONDUCTOR NANOCRYSTAL CAPABLE OF EMITTING, ABSORBING, SCATTERING, OR DIFFRACTING ENERGY IN A NARROW FREQUENCY BAND WHEN EXCITED;

2. AN AFFINITY MOLECULE CAPABLE OF BONDING TO THE DETECTABLE SUBSTANCE; AND

3. ONE OR MORE LINKING AGENTS CAPABLE OF LINKING TO BOTH THE SEMICONDUCTOR NANOCRYSTAL AND THE AFFINITY MOLECULE

↓

REMOVING FROM THE BIOLOGICAL MATERIAL PORTIONS OF THE ORGANO LUMINESCENT SEMICONDUCTOR NANOCRYSTAL PROBE NOT BONDED TO THE DETECTABLE SUBSTANCE

↓

EXPOSING THE BIOLOGICAL MATERIAL TO ENERGY CAPABLE OF EXCITING THE SEMICONDUCTOR NANOCRYSTAL IN ANY ORGANO-LUMINESCENT DETECTION COMPOUND PRESENT IN THE BIOLOGICAL MATERIAL TO EMIT, ABSORB, SCATTER OR DIFFRACT ENERGY

↓

DETECTING ANY ENERGY EMITTED AND/OR ANY ABSORBED, AND/OR SCATTERED OR DIFFRACTED BY THE SEMICONDUCTOR NANOCRYSTAL INDICATING THE PRESENCE IN THE BIOLOGICAL MATERIAL OF ANY DETECTABLE SUBSTANCE BONDED TO THE ORGANO-LUMINESCENT DETECTION COMPOUND

ORGANO LUMINESCENT SEMICONDUCTOR NANOCRYSTAL PROBES FOR BIOLOGICAL APPLICATIONS AND PROCESS FOR MAKING AND USING SUCH PROBES

BACKGROUND OF THE INVENTION

The invention described herein arose in the course of, or under, Contract No. DE-AC03-SF00098 between the United States Department of Energy and the University of California for the operation of the Ernest Orlando Lawrence Berkeley National Laboratory. The Government may have rights to the invention.

1. Field of the Invention

This invention relates to organo luminescent semiconductor nanocrystal probes for biological applications wherein the probes includes a plurality of semiconductor nanocrystals capable of luminescence and/or absorption and/or scattering or diffraction when excited by a radiation or particle beam.

2. Description of the Related Art

Fluorescent labeling of biological systems is a well known analytical tool used in modern biotechnology as well as analytical chemistry. Applications for such fluorescent labeling include technologies such as medical (and nonmedical) fluorescence microscopy, histology, flow cytometry, fluorescence in-situ hybridization (medical assays and research), DNA sequencing, immuno-assays, binding assays, separation, etc.

Conventionally, such fluorescent labeling involves the use of an organic dye molecule bonded to a moiety which, in turn, selectively bonds to a particular biological system, the presence of which is then identified by excitation of the dye molecule to cause it to fluoresce. There are a number of problems with such an analytical system. In the first place, the emission of light of visible wavelengths from an excited dye molecule usually is characterized by the presence of a broad emission spectrum as well as a broad tail of emissions on the red side of the spectrum, i.e., the entire emission spectrum is rather broad. As a result, there is a severe limitation on the number of different color organic dye molecules which may be utilized simultaneously or sequentially in an analysis since it is difficult to either simultaneously or even non-simultaneously detect or discriminate between the presence of a number of different detectable substances due to the broad spectrum emissions and emission tails of the labelling molecules. Another problem is that most dye molecules have a relatively narrow absorption spectrum, thus requiring either multiple excitation beams used either in tandem or sequentially for multiple wavelength probes, or else a broad spectrum excitation source which is sequentially used with different filters for sequential excitation of a series of probes respectively excited at different wavelengths.

Another problem frequently encountered with existing dye molecule labels is that of photostability. Available fluorescent molecules bleach, or irreversibly cease to emit light, under repeated excitation ($10^4$–$10^8$) cycles of absorption/emission. These problems are often surmounted by minimizing the amount of time that the sample is exposed to light, and by removing oxygen and/or other radical species from the sample.

In addition, the probe tools used for the study of these systems by electron microscopy techniques are completely different from the probes used for study by fluorescence. Thus, it is not possible to label a material with a single type of probe for both electron microscopy and for fluorescence.

It would, therefore, be desirable to provide a stable probe material for biological applications having a wide absorption band and capable of exhibiting either a detectable change in absorption or of emitting radiation in a narrow wavelength band, without the presence of the large red emission tails characteristic of dye molecules (thereby permitting the simultaneous use of a number of such probe materials, each emitting light of a different narrow wavelength band) and/or capable of scattering or diffracting radiation. It would also be equally desirable to provide a single, stable probe material which can be used to image the same sample by both light and electron microscopy.

SUMMARY OF THE INVENTION

The invention comprises a luminescent semiconductor nanocrystal compound capable of linking to an affinity molecule to form an organo luminescent semiconductor nanocrystal probe capable of luminescence and/or absorption and/or scattering or diffracting when excited by an electromagnetic radiation source (of broad or narrow bandwidth) or a particle beam, and capable of exhibiting a detectable change in absorption and/or of emitting radiation in a narrow wavelength band and/or scattering or diffracting when so excited. The luminescent semiconductor nanocrystal compound preferably comprises: (1) a semiconductor nanocrystal capable of luminescence and/or absorption and/or scattering or diffraction when excited by an electromagnetic radiation source (of broad or narrow bandwidth) or a particle beam, and capable of exhibiting a detectable change in absorption and/or of emitting radiation in a narrow wavelength band and/or scattering or diffracting when excited; and (2) a linking agent having a first portion linked to the semiconductor nanocrystal, and a second portion capable of linking to an affinity molecule.

The invention further comprises an organo luminescent semiconductor nanocrystal probe formed by linking the above described luminescent semiconductor nanocrystal compound to an affinity molecule capable of bonding to a detectable substance in a material. As a result the organo luminescent semiconductor nanocrystal probe, in one embodiment, is capable of absorbing or scattering or diffracting energy from either a particle beam or an electromagnetic radiation source (of broad or narrow bandwidth), and is capable of emitting electromagnetic radiation in a narrow wavelength band when so excited; while in another embodiment the amount of energy so absorbed, or scattered, or diffracted from either a particle beam or an electromagnetic radiation source (of broad or narrow bandwidth), is detectable, i.e., the change in absorption, scattering, or diffraction is detectable.

Therefore, treatment of a material with the organo luminescent semiconductor nanocrystal probe, and subsequent exposure of this treated material to excitation energy (from either a particle beam or an electromagnetic radiation source of broad or narrow bandwidth) to determine the presence of the detectable substance within the material, will excite the semiconductor nanocrystals in the organo luminescent semiconductor nanocrystal probe bonded to the detectable substance, resulting in the emission of electromagnetic radiation of a narrow wavelength band and/or a detectable change in the amount of energy being absorbed and/or scattered or diffracted, signifying the presence, in the material, of the detectable substance bonded to the organo luminescent semiconductor nanocrystal probe.

The invention also comprises a process for making the luminescent semiconductor nanocrystal compound and for making the organo luminescent semiconductor nanocrystal probe comprising the luminescent semiconductor nanocrystal compound linked to an affinity molecule capable of bonding to a detectable substance. The organo luminescent semiconductor nanocrystal probe of the invention is stable with respect to repeated excitation by light, or exposure to oxygen or other radicals. The invention further comprises a process for treating a material, such as a biological material, to determine the presence of a detectable substance in the material which comprises contacting the material with the organo luminescent semiconductor nanocrystal probe, removing from the material portions of the organo luminescent semiconductor nanocrystal probe not bonded to the detectable substance, and then exposing the material to activation energy from either an electromagnetic radiation source (of broad or narrow bandwidth) or a particle beam. The presence of the detectable substance in the material is then determined either by measuring the absorption of energy by the organo luminescent semiconductor nanocrystal probe and/or detecting the emission of radiation of a narrow wavelength band by the organo luminescent semiconductor nanocrystal probe and/or detecting the scattering or diffraction by the organo luminescent semiconductor nanocrystal probe, indicative (in either case) of the presence of the organo luminescent semiconductor nanocrystal probe bonded to the detectable substance in the material.

BRIEF DESCRIPTION OF THE DRAWINGS

FIG. 4 is a flow sheet illustrating the process of forming the organo luminescent semiconductor nanocrystal probe of the invention.

FIG. 5 is a flow sheet illustrating a typical use of the organo luminescent semiconductor nanocrystal probe of the invention in detecting the presence of a detectable substance in a material such as a biological material.

DETAILED DESCRIPTION OF THE INVENTION

Figure 1:
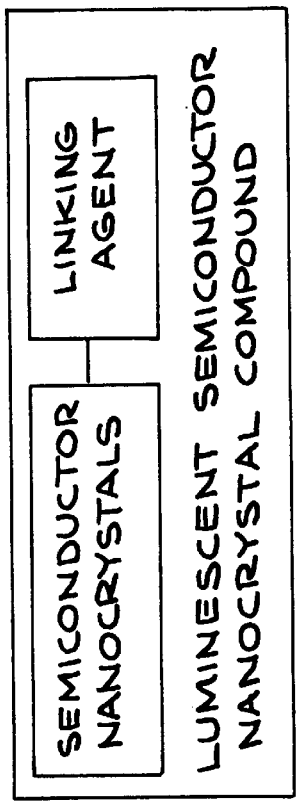
FIG. 1 is a block diagram of the luminescent semiconductor nanocrystal compound of the invention.
Figure 2:
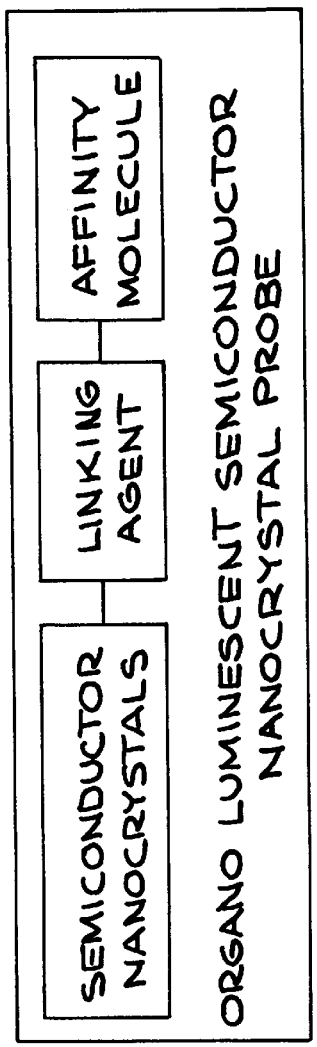
FIG. 2 is a block diagram of the organo luminescent semiconductor nanocrystal probe of the invention.
Figure 3:
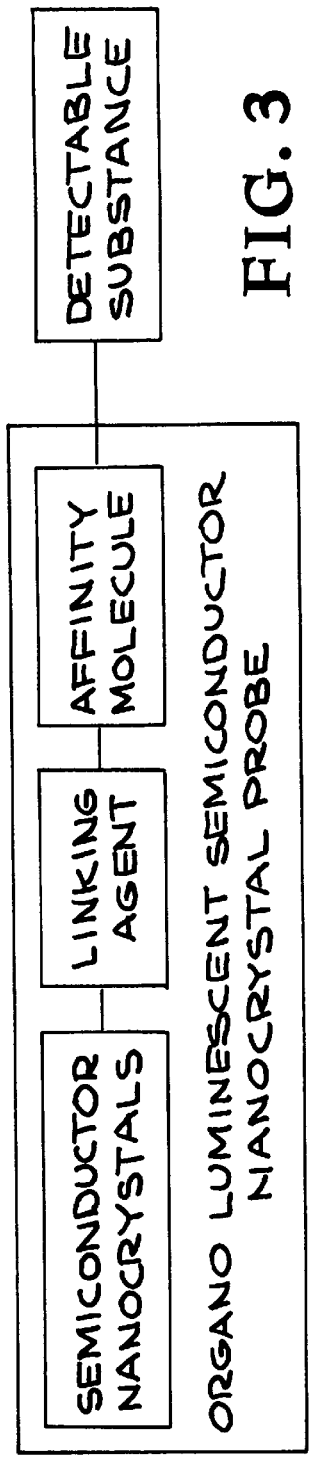
FIG. 3 is a block diagram showing the affinity between a detectable substance and the organo luminescent semiconductor nanocrystal probe of the invention.

The invention comprises a luminescent semiconductor nanocrystal compound capable of linking to an organic molecule and capable of exhibiting a detectable change in absorption and/or of emitting electromagnetic radiation in a narrow wavelength band and/or scattering or diffracting when excited by either an electromagnetic radiation source (of broad or narrow bandwidth) or a particle beam. The luminescent semiconductor nanocrystal compound, in turn, comprises: (1) semiconductor nanocrystals capable of exhibiting a detectable change in absorption and/or of emitting electromagnetic radiation in a narrow wavelength band when excited by either an electromagnetic radiation source (of broad or narrow bandwidth) or a particle beam; and (2) one or more linking agents each having a first portion linked to the semiconductor nanocrystal and a second portion capable of linking to an organic affinity molecule.

The invention also comprises the above described luminescent semiconductor nanocrystal compound linked to the organic affinity molecule (through the linking agent) to form an organo luminescent semiconductor nanocrystal probe capable of bonding to a detectable substance and capable of exhibiting a detectable change in absorption and/or of emitting electromagnetic radiation in a narrow wavelength band and/or scattering or diffracting when excited by either an electromagnetic radiation source (of broad or narrow bandwidth) or a particle beam. Treatment of a material (typically a biological material) with the organo luminescent semiconductor nanocrystal probe, and subsequent exposure of this treated material to excitation energy, as described above, to determine the presence of the detectable substance within the material, will excite the semiconductor nanocrystal in the organo luminescent semiconductor nanocrystal probe bonded to the detectable substance, causing the detectable change in absorption and/or emission of electromagnetic radiation of a narrow wavelength band and/or scattering or diffraction signifying (in either instance) the presence in the material, of the detectable substance bonded to the organo luminescent semiconductor nanocrystal probe.

The invention also comprises a process for making the luminescent semiconductor nanocrystal compound, and a process for making the organo luminescent semiconductor nanocrystal probe comprising the luminescent semiconductor nanocrystal compound linked to an affinity molecule capable of bonding to a detectable substance.

The invention further comprises a process for treating a material, such as a biological material, to determine the presence of a detectable substance in the material which comprises: (1) contacting the material with the organo luminescent semiconductor nanocrystal probe, (2) removing from the material portions of the organo luminescent semiconductor nanocrystal probe not bonded to the detectable substance, (3) exposing the material to energy (such as the above-described electromagnetic energy source or particle beam) capable of exciting the semiconductor nanocrystal to cause a detectable change in absorption and/or emission of electromagnetic radiation of a narrow wavelength band and/or scattering or diffraction signifying (in either instance) the presence of the organo luminescent semiconductor nanocrystal probe bonded to the detectable substance in the material, and (4) detecting either the change in absorbed energy or the electromagnetic radiation emitted or the scattering or diffraction by the semiconductor nanocrystal in the organo luminescent semiconductor nanocrystal probe.

a. Definitions

By use of the terms "nanometer crystal" or "nanocrystal" herein is meant an organic or inorganic single crystal particle having an average cross-section no larger than about 20 nanometers (nm) or $20 \times 10^{-9}$ meters (200 Angstroms), preferably no larger than about 10 nm (100 Angstroms) and a minimum average cross-section of about 1 nm, although in some instances a smaller average cross-section nanocrystal, i.e., down to about 0.5 nm (5 Angstroms), may be acceptable. Typically the nanocrystal will have an average cross-section ranging in size from about 1 nm (10 Angstroms) to about 10 nm (100 angstroms).

By use of the term "semiconductor nanocrystal" is meant a nanometer crystal or nanocrystal of Group II–VI and Group III–V semiconductor compounds capable of emitting electromagnetic radiation upon excitation, although the use of Group IV semiconductors such as germanium or silicon, or the use of organic semiconductors, may be feasible under certain conditions.

By use of the term "a narrow wavelength band", with regard to the electromagnetic radiation emission of the semiconductor nanocrystal, is meant a wavelength band of emissions not exceeding about 40 nm, and preferably not exceeding about 20 nm in width and symmetric about the center, in contrast to the emission bandwidth of about 100 nm for a typical dye molecule, with a red tail which may extend the band width out as much as another 100 nm. It should be noted that the bandwidths referred to are determined from measurement of the width of the emissions at half peak height (FWHM), and are appropriate in the range of 200 nm to 2000 nm.

By use of the term "a broad absorption band", with regard to the electromagnetic radiation absorption of the semiconductor nanocrystal is meant a continuously increasing absorption from the onset, which occurs near to, but at slightly higher energy than the "narrow wavelength band" of the emission. This is in contrast to the "narrow absorption band" of dye molecules which occurs near the emission peak on the high energy side, but drops off rapidly away from that wavelength.

By use of the term "detectable substance" is meant an entity or group, the presence or absence of which in a material such as a biological material, is to be ascertained by use of the organo luminescent semiconductor nanocrystal probe of the invention.

By use of the term "affinity molecule" is meant the portion of the organo luminescent semiconductor nanocrystal probe of the invention which will selectively bond to a detectable substance (if present) in the material (e.g., biological material) being analyzed.

By use of the term "linking agent" is meant a substance capable of linking with a semiconductor nanocrystal and also capable of linking to an affinity molecule.

The terms "link" and "linking" are meant to describe the adherence between the affinity molecule and the semiconductor nanocrystals, either directly or through a moiety identified herein as a linking agent. The adherence may comprise any sort of bond, including, but not limited to, covalent, ionic, hydrogen bonding, Van der Waals' forces, or mechanical bonding, etc.

The terms "bond" and "bonding" are meant to describe the adherence between the affinity molecule and the detectable substance. The adherence may comprise any sort of bond, including, but not limited to, covalent, ionic, or hydrogen bonding, Van der Waals' forces, or mechanical bonding, etc.

The term "luminescent semiconductor nanocrystal compound", as used herein, is intended to define a semiconductor nanocrystal linked to one or more linking agents and capable of linking to an affinity molecule, while the term "organo-luminescent semiconductor nanocrystal probe" is intended to define a luminescent semiconductor nanocrystal compound linked to an affinity molecule.

The term "glass" as used herein is intended to include one or more oxides of silicon, boron, and/or phosphorus, or a mixture thereof, as well as the further optional inclusion of one or more metal silicates, metal borates or metal phosphates therein.

b. The Semiconductor Nanocrystals

The semiconductor nanocrystals useful in the practice of the invention include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe; and nanocrystals of Group III–V semiconductors such as GaAs, InGaAs, InP, and InAs.

As mentioned above, the use of Group IV semiconductors such as germanium or silicon, or the use of organic semiconductors, may also be feasible under certain conditions.

Formation of nanometer crystals of Group III–V semiconductors is described in copending and commonly assigned Alivisatos et al. U.S. Pat. No. 5,251,018; Alivisatos et al. U.S. Pat. No. 5,505,928; and Alivisatos et al. U.S. Pat. No. 5,262,357, which also describes the formation of Group II–VI semiconductor nanocrystals, and which is also assigned to the assignee of this invention. Also described therein is the control of the size of the semiconductor nanocrystals during formation using crystal growth terminators. The teachings of Alivisatos et al. Pat. No. 5,751,018, and Alivisatos et al. U.S. Pat. No. 5,262,357 are each hereby specifically incorporated by reference.

In a preferred embodiment, the nanocrystals are used in a core/shell configuration wherein a first semiconductor nanocrystal forms a core ranging in diameter, for example, from about 20 Å to about 100 Å, with a shell of another semiconductor nanocrystal material grown over the core nanocrystal to a thickness of, for example, 1–10 monolayers in thickness. When, for example, a 1–10 monolayer thick shell of CdS is epitaxially grown over a core of CdSe, there is a dramatic increase in the room temperature photoluminescence quantum yield. Formation of such core/shell nanocrystals is described more fully in a publication by one of us with others entitled "Epitaxial Growth of Highly Luminescent CdSe/CdS Core/Shell Nanocrystals with Photostability and Electronic Accessibility", by Peng, Schlamp, Kadavanich, and Alivisatos, published in the Journal of the American Chemical Society, Volume 119, No. 30. 1997, at pages 7019–7029, the subject matter of which is hereby specifically incorporated herein by reference.

The semiconductor nanocrystals used in the invention will have a capability of emitting light within a narrow wavelength band of about 40 nm or less, preferably about 20 nm or less, thus permitting the simultaneous use of a plurality of differently colored organo luminescent semiconductor nanocrystal probes with different semiconductor nanocrystals without overlap (or with a small amount of overlap) in wavelengths of emitted light (unlike the use of dye molecules with broad emission lines (e.g.,~100 nm) and broad tails of emission (e.g., another 100 nm) on the red side of the spectrum), thus allowing for the simultaneous detection of a plurality of detectable substances.

c. Affinity Molecule

The particular affinity molecule forming a part of the organo-luminescent semiconductor nanocrystal probe of the invention will be selected based on its affinity for the particular detectable substance whose presence or absence, for example, in a biological material, is to be ascertained. Basically, the affinity molecule may comprise any molecule capable of being linked to a luminescent semiconductor nanocrystal compound which is also capable of specific recognition of a particular detectable substance. In general, any affinity molecule useful in the prior art in combination with a dye molecule to provide specific recognition of a detectable substance will find utility in the formation of the organo-luminescent semiconductor nanocrystal probes of the invention. Such affinity molecules include, by way of example only, such classes of substances as monoclonal and polyclonal antibodies, nucleic acids (both monomeric and oligomeric), proteins, polysaccharides, and small molecules such as sugars, peptides, drugs, and ligands. Lists of such affinity molecules are available in the published literature such as, by way of example, the "Handbook of Fluorescent Probes and Research Chemicals", (sixth edition) by R. P. Haugland, available from Molecular Probes, Inc.

d. The Linking Agent

The organo-luminescent semiconductor nanocrystal probe of the invention will usually find utility with respect to the detection of one or more detectable substances in organic materials, and in particular to the detection of one or more detectable substances in biological materials. This requires the presence, in the organo-luminescent semiconductor nanocrystal probe, of an affinity molecule or moiety, as described above, which will bond the organo-luminescent semiconductor nanocrystal probe to the detectable substance in the organic/biological material so that the presence of the detectable material may be subsequently ascertained. However, since the semiconductor nanocrystals are inorganic, they may not bond directly to the organic affinity molecule. In these case therefore, there must be some type of linking agent present in the organo-luminescent semiconductor nanocrystal probe which is capable of forming a link to the inorganic semiconductor nanocrystal as well as to the organic affinity molecule in the organo-luminescent semiconductor nanocrystal probe.

One form in which the semiconductor nanocrystal may be linked to an affinity molecule via a linking agent is by coating the semiconductor nanocrystal with a thin layer of glass, such as silica ($SiO_x$ where x=1–2), using a linking agent such as a substituted silane, e.g., 3-mercaptopropyl-trimethoxy silane to link the nanocrystal to the glass. The glass-coated semiconductor nanocrystal may then be further treated with a linking agent, e.g., an amine such as 3-aminopropyl-trimethoxysilane, which will function to link the glass-coated semiconductor nanocrystal to the affinity molecule. That is, the glass-coated semiconductor nanocrystal may then be linked to the affinity molecule. It is within the contemplation of this invention that the original luminescent semiconductor nanocrystal compound may also be chemically modified after it has been made in order to link effectively to the affinity molecule. A variety of references summarize the standard classes of chemistry which may be used to this end, in particular the "Handbook of Fluorescent Probes and Research Chemicals", (6th edition) by R. P. Haugland, available from Molecular Probes, Inc., and the book "Bioconjugate Techniques", by Greg Hermanson, available from Academic Press, New York.

When the semiconductor nanocrystal is coated with a thin layer of glass, the glass, by way of example, may comprise a silica glass ($SiO_x$ where x=1–2), having a thickness ranging from about 0.5 nm to about 10 nm, and preferably from about 0.5 nm to about 2 nm.

The semiconductor nanocrystal is coated with the coating of thin glass, such as silica, by first coating the nanocrystals with a surfactant such as tris-octyl-phosphine oxide, and then dissolving the surfactant-coated nanocrystals in a basic methanol solution of a linking agent, such as 3-mercaptopropyl-tri-methoxy silane, followed by partial hydrolysis which is followed by addition of a glass-affinity molecule linking agent such as amino-propyl trimethoxysilane which will link to the glass and serve to form a link with the affinity molecule.

When the linking agent does not involve the use of a glass coating on the semiconductor nanocrystal, it may comprise a number of different materials, depending upon the particular affinity molecule, which, in turn, depends upon the type of detectable material being analyzed for. It should also be noted that while an individual linking agent may be used to link to an individual semiconductor nanocrystal, it is also within the contemplation of the invention that more than one linking agent may bond to the same semiconductor nanocrystal and vice versa.

A few examples of the types of linking agents which may be used to link to both the semiconductor nanocrystal (or to a glass coating on the nanocrystal) and to the organic affinity molecule in the probe are illustrated in the table below, it being understood that this is not intended to be an exhaustive list:

Linking Agent

| Structure | Name |
|---|---|
| (structure with HS—phenyl—C(=O)—NH—CH₂CH₂CH₂—NH₂) | N-(3-aminopropyl)3-mercapto-benzamide |
| (CH₃O)₃Si–CH₂CH₂CH₂–NH₂ | 3-aminopropyl-trimethoxysilane |
| (CH₃O)₃Si–CH₂CH₂CH₂–SH | 3-mercaptopropyl-trimethoxysilane |
| (CH₃O)₃Si–CH₂CH₂CH₂–maleimide | 3-maleimidopropyl-trimethoxysilane |
| (CH₃O)₃Si–CH₂CH₂CH₂–C(=O)–NH–NH₂ | 3-hydrazidopropyl-trimethoxysilane |

It should be further noted that a plurality of polymerizable linking agents may be used together to form an encapsulating net or linkage around an individual nanocrystal (or group of nanocrystals). This is of particular interest where the particular linking agent is incapable of forming a strong bond with the nanocrystal. Examples of linking agents capable of bonding together in such a manner to surround the nanocrystal with a network of linking agents include, but are not limited to: diacetylenes, acrylates, acrylamides, vinyl, styryl, and the aforementioned silicon oxide, boron oxide, phosphorus oxide, silicates, borates and phosphates.

e. The Excitation of the Probe and Detection of Emission/Absorption

As previously mentioned, the organo luminescent semiconductor nanocrystal probe of the invention is capable of being excited over a broad bandwidth, yet exhibits emission in a narrow wavelength band, in contrast to the dye molecules used in the prior art. Thus electromagnetic radiation of wavelength ranging from x-ray to ultraviolet to visible to infrared waves may be used to excite the luminescent semiconductor nanocrystals in the probe. In addition, the luminescent semiconductor nanocrystals are capable of excitation from bombardment with a particle beam such as an electron beam (e-beam). Furthermore, because of the broad bandwidth at which the luminescent semiconductor nanocrystals are excitable, one may use a common excitation source for the simultaneous excitation of several probes, i.e., several probes which give off radiation at different frequencies, thus permitting simultaneous excitation and detection of the presence of several probes indicating, for example, the presence of several detectable substances in the material being examined.

Thus, for example, a laser radiation source of a given frequency, e.g., blue light, may be used to excite a first organo luminescent semiconductor nanocrystal probe capable of emitting radiation of a second frequency, e.g., red light, indicating the presence, in the material being illuminated, of a first detectable substance to which the particular red light-emitting organo luminescent semiconductor nanocrystal probe has bonded. At the same time, the same blue light laser source may also be exciting a second organo luminescent semiconductor nanocrystal probe (in the same material) capable of emitting radiation of a third frequency, e.g., green light, indicating the presence, in the material being illuminated, of a second detectable substance to which the particular green light-emitting organo luminescent semiconductor nanocrystal probe has bonded. Thus, unlike the prior art, multiple excitation sources need not be used (because of the broad bandwidth in which the organo luminescent semiconductor nanocrystal probe of the invention is capable of being excited), and the narrow band of emission of the specific semiconductor nanocrystals in each probe makes possible the elimination of sequencing and/or elaborate filtering to detect the emitted radiation.

With respect to the absorption of energy by the probe of the invention, when the excitation source is an electron beam, or an X-ray source, the presence of the organo luminescent semiconductor nanocrystal probe bonded to the detectable substance of interest in the material being analyzed can be ascertained using a commercially available energy absorption or scattering or diffraction detection system wherein changes in absorption or scattering cross section or in diffraction of the material being analyzed can be detected, signifying the presence of the probe in the material, which, in turn, indicates the presence of the detectable substance to which the probe is bonded in the material being analyzed. In addition, it may be possible to use electron or X-ray sources to detect the presence of the organo luminescent semiconductor nanocrystal probe bonded to the detectable substance by using a conventional detection system for the emission of visible light to observe the visible emission in the narrow wavelength of emission of the probe.

The following examples will serve to further illustrate the formation of the organo luminescent semiconductor nanocrystal probes of the invention, as well as their use in detecting the presence of a detectable substance in a material such as a biological material.

EXAMPLE 1

To illustrate the formation of the luminescent semiconductor nanocrystal compound (comprising the semiconductor nanocrystals linked to a linking agent) 20 ml. of a 5 mM solution of (4-mercapto)benzoic acid was prepared with a pH of 10 using $(CH_3)_4NOH.5H_2O$. 20 mg of tris-octylphosphine oxide coated CdSe/CdS core/shell nanocrystals were added to the solution and stirred until completely dissolved. The resultant nanocrystal/linking agent solution was heated for 5 hours at 50–60° C. and then concentrated to a few ml by evaporation. Then an equal volume of acetone was added and the nanocrystals precipitate out of solution homogeneously. The precipitate was then washed with acetone, dried, and then can be stored.

The luminescent semiconductor nanocrystal compound prepared above can be linked with an appropriate affinity molecule to form the organo luminescent semiconductor nanocrystal probe of the invention to treat a biological material to determine the presence or absence of a detectable substance. That is, the luminescent semiconductor nanocrystal compound prepared above can be linked, for example, with avidin or streptavidin (as the affinity molecule) to form an organo luminescent semiconductor nanocrystal probe to treat a biological material to ascertain the presence of biotin; or the luminescent semiconductor nanocrystal compound prepared above can be linked with anti-digoxiginen to form an organo luminescent semiconductor nanocrystal probe to treat a biological material to ascertain the presence of digoxiginen.

EXAMPLE 2

To illustrate the formation of luminescent semiconductor nanocrystal compound (comprising glass-coated semiconductor nanocrystals linked to a linking agent), 50 $\mu l$ of 3-mercaptopropyl-trimethoxy silane was added to 40 ml of an anhydrous solution of 25 vol. % dimethylsulfoxide in methanol, and the pH was adjusted to 10–11 using $(CH_3)_4NOH.5H_2O$. 10 mg of tris-octylphosphine oxide coated CdSe/CdS core-shell particles, prepared by the technique described in the aforementioned Peng, Schlamp, Kadavanich, and Alivisatos article, were then dissolved in this solution, and stirred for several hours. The solution was diluted with 40 ml of methanol adjusted to a pH of 10 with $(CH_3)_4NOH.5H_2O$, and heated for 1 hour at 69° C. The solution was stirred for an hour, and 40 ml of a 90 vol. % methanol/9.89 vol. % $H_2O$/0.1 vol. % trimethoxysilylpropyl urea/0.01 vol. % aminopropyl-trimethoxy silane solution which had been stirring for at least an hour, was added, and stirred for 2 hours. Subsequently the reaction was heated to 69° C. for 15 minutes, and then cooled. 10 ml of a 10 vol. % chlorotrimethyl silane solution in methanol which had been adjusted to a pH of 10 using $(CH_3)_4NOH.5H_2O$ was added, stirred for 2 hours, then heated to 60° C., and then partially concentrated under vacuum. Once the methanol had all evaporated, the solution was precipitated with acetone as an oil product comprising the luminescent semiconductor nanocrystal compound. The luminescent semiconductor nanocrystal compound may then be redissolved in water, and in a variety of buffer solutions to prepare it for linking it to an affinity molecule to form the organo luminescent semiconductor nanocrystal probe of the invention to treat a biological material to determine the presence or absence of a detectable substance.

Thus, the invention provides an organo luminescent semiconductor nanocrystal probe containing a semiconductor nanocrystal capable, upon excitation by either electromagnetic radiation (of either narrow or broad bandwidth) or particle beam, of emitting electromagnetic radiation in a narrow wavelength band and/or absorbing energy and/or scattering or diffracting said excitation, thus permitting the simultaneous usage of a number of such probes emitting different wavelengths of electromagnetic radiation to thereby permit simultaneous detection of the presence of a number of detectable substances in a given material. The probe material is stable in the presence of light or oxygen, capable of being excited by energy over a wide spectrum, and has a narrow band of emission, resulting in an improved material and process for the simultaneous and/or sequential detection of a number of detectable substances in a material such as a biological material.

Having thus described the invention what is claimed is:

1. A luminescent semiconductor nanocrystal compound capable of linking to an affinity molecule and capable of emitting electromagnetic radiation in a narrow wavelength band when excited comprising:
   a) a semiconductor nanocrystal capable of emitting light in a narrow wavelength band when excited; and
   b) one or more linking agent linked to said semiconductor nanocrystal and capable of linking to said affinity molecule.

2. The luminescent semiconductor nanocrystal compound of claim 1 wherein said semiconductor nanocrystal is capable of absorbing energy over a wide bandwidth.

3. The luminescent semiconductor nanocrystal compound of claim 1 wherein said linking agent includes a glass coating on said semiconductor nanocrystal capable of being linked to said affinity molecule through a further linking agent capable of linking to both said glass coating and said affinity molecule.

4. The luminescent semiconductor nanocrystal compound of claim 3 wherein said glass coating on said semiconductor nanocrystal comprises a coating of silica glass.

5. The luminescent semiconductor nanocrystal compound of claim 1 wherein said linking agent comprise a first portion linked to said semiconductor nanocrystal and a second portion capable of linking to said affinity molecule.

6. The luminescent semiconductor nanocrystal compound of claim 1 wherein said one or more lining agents comprise:
   a) a glass coating on said semiconductor nanocrystal; and
   b) a further linking agent having a first portion linked to said glass coating on said semiconductor nanocrystal and a second portion capable of linking to said affinity molecule.

7. An organo luminescent semiconductor nanocrystal probe capable of bonding with a detectable substance and capable of emitting electromagnetic radiation in a narrow wavelength band when excited, comprising a luminescent semiconductor nanocrystal compound linked to an affinity molecule capable of bonding to said detectable substance.

8. An organo luminescent semiconductor nanocrystal probe capable of bonding with a detectable substance and capable of emitting electromagnetic radiation in a narrow wavelength band when excited comprising:
   a) a semiconductor nanocrystal capable of emitting electromagnetic radiation in a narrow wavelength band when excited;
   b) at least one linking agent linked to said semiconductor nanocrystal and having a second portion capable of linking to an affinity molecule; and
   c) an affinity molecule linked to said second portion of said linking agent, and capable of selectively bonding to said detectable substance;

whereby treatment of a material with said organo luminescent semiconductor nanocrystal probe, and subsequent exposure of said treated material to excitation energy to determine the presence of said detectable substance within said material will excite said semiconductor nanocrystal in said organo luminescent semiconductor nanocrystal probe bonded to said detectable substance causing the emission of electromagnetic radiation of a narrow wavelength band signifying the presence, in said material, of said detectable substance bonded to said organo luminescent semiconductor nanocrystal probe.

9. The organo luminescent semiconductor nanocrystal probe of claim 8 wherein said linking agent comprises a glass coating on said semiconductor nanocrystal.

10. The organo luminescent semiconductor nanocrystal probe of claim 8 wherein said material treated with said organo luminescent semiconductor nanocrystal probe to determine the presence of said detectable substance comprises a biological material.

11. The organo luminescent semiconductor nanocrystal probe of claim 8 wherein said material treated with said organo luminescent semiconductor nanocrystal probe to determine the presence of said detectable substance comprises an organic material.

12. The organo luminescent semiconductor nanocrystal probe of claim 8 wherein said material treated with said organo luminescent semiconductor nanocrystal probe to determine the presence of said detectable substance comprises an inorganic material.

13. A process for forming a luminescent semiconductor nanocrystal compound capable of lining to an affinity molecule and capable of emitting electromagnetic radiation in a narrow wavelength band when excited which comprises: linking together a semiconductor nanocrystal capable of emitting electromagnetic radiation in a narrow wavelength band when excited and a linking agent having a first portion linked to said semiconductor nanocrystal and a second portion capable of linking to an affinity molecule.

14. The process of claim 13 which further comprises forming a glass coating on said semiconductor nanocrystal and then treating said glass with said linking agent having said second portion capable of linking with an affinity molecule, whereby said first portion of said linking agent links to said semiconductor nanocrystal via said class.

15. A process for forming an organo luminescent semiconductor nanocrystal probe capable of bonding with a detectable substance and capable of emitting electromagnetic radiation in a narrow wavelength band when excited which comprises linking a luminescent semiconductor nanocrystal compound with an affinity molecule capable of bonding with a detectable substance.

16. A process for forming an organo luminescent semiconductor nanocrystal probe capable of bonding with a detectable substance and capable of emitting electromagnetic radiation in a narrow wavelength band when excited which comprises the steps of:
   a) linking a semiconductor nanocrystal capable of emitting electromagnetic radiation in a narrow wavelength band when excited with a linking agent having a first portion linked to said semiconductor nanocrystal and a second portion capable of linking to an affinity molecule; and
   b) linking said linking agent and an affinity molecule capable of bonding with said detectable substance.

17. The process of claim 16 wherein said step of linking together said semiconductor nanocrystal and said linking agent is carried out prior to said step of linking together said linking agent and said affinity molecule.

18. The process of claim 16 wherein said step of linking together said linking agent and said affinity molecule is carried out prior to said step of linking together said semiconductor nanocrystal and said linking agent.

19. The process of claim 16 wherein said step of linking together said semiconductor nanocrystal and said linking agent further comprises coating said semiconductor nanocrystal with a glass and then treating said glass-coated semiconductor nanocrystal with said linking agent capable of linking to said affinity molecule, whereby said first portion of said linking agent lihs to said semiconductor nanocrystal via said glass and said second portion links to said affinity molecule.

20. A process for treating a material to determine the presence of one or more detectable substances in said material which comprises:
   a) contacting said material with a first organo luminescent semiconductor nanocrystal probe capable of bonding with a first detectable substance, if present, in said material, and capable of emitting electromagnetic radiation in a first narrow wavelength band when excited, said first organo luminescent semiconductor nanocrystal probe comprising:
      i) a first semiconductor nanocrystal capable of being excited over a broad bandwidth and capable of emitting electromagnetic radiation in said first narrow wavelength band when excited;
      ii) an affinity molecule capable of selectively bonding to said detectable substance; and
      iii) a linking agent linked to said first semiconductor nanocrystal and also linked to said affinity molecule;
   b) removing, from said material, portions of said first organo luminescent semiconductor nanocrystal probe not bonded to said first detectable substance; and
   c) exposing said material to energy capable of exciting said first semiconductor nanocrystal to emit electromagnetic radiation in said first narrow wavelength band, indicative of the presence of said first detectable substance in said material; and
   d) detecting said electromagnetic radiation in said first narrow wavelength band emitted by said first semiconductor nanocrystal in said first organo luminescent semiconductor nanocrystal probe.

21. The process of claim 20 which includes the further step of treating said material with at least a second organo luminescent semiconductor nanocrystal probe capable of bonding to an additional detectable substance in said material, and containing a second semiconductor nanocrystal capable of being excited over a broad bandwidth and capable of emitting electromagnetic radiation in a second narrow wavelength band different from said first narrow wavelength band, whereby the exposure of said material to energy capable of exciting both said first and second nanocrystals will cause any of said first or second semiconductor nanocrystals present in said material to emit electromagnetic radiation of differing narrow wavelength bands, whereby the presence or absence of more than one detectable substance in a material may be simultaneously detected using a single excitation energy source.

22. The process of claim 21 wherein at least one further organo luminescent semiconductor nanocrystal probe is used to treat said material, with each of said organo luminescent semiconductor nanocrystal probes selectively bondable to a different detectable substance and each of said organo luminescent semiconductor nanocrystal probes capable of being excited over a broad bandwidth and capable of emitting electromagnetic radiation of a different narrow wavelength band, whereby a plurality of detectable substances may be simultaneously analyzed for in a material using a single excitation source.

23. The process of claim 21 wherein said material is treated with all of said organo luminescent semiconductor nanocrystal probes prior to said step of removing, from said material, portions of said first organo luminescent semiconductor nanocrystal probe not bonded to said first detectable substance, and said step of removing further comprises removing portions of all of said organo luminescent semiconductor nanocrystal probes not bonded to a detectable substance in said material.

24. The process of claim 21 whereby the exposure of the material to light of a selected wavelength is used to excite selectively one or more, but not all, of said organo luminescent semiconductor nanocrystal probes, thus allowing identification of the presence of specific labelled detectable substances, or subsets of different labelled detectable substances in said material.

25. The process for treating a material of claim 20 wherein said material comprises a biological material.

26. The process for treating a material of claim 20 wherein said step of exposing said material to energy capable of exciting said first semiconductor nanocrystal to emit electromagnetic radiation further comprises exposing said material to a source of electromagnetic radiation capable of emitting photons of a broad or narrow spectrum.

27. The process for treating a material of claim 20 wherein said step of exposing said material to energy capable of exciting said first semiconductor nanocrystal to emit electromagnetic radiation further comprises exposing said material to an electron beam.

28. A process for treating a material to determine the presence of a detectable substance in said material which comprises:
   a) contacting said material with an organo luminescent semiconductor nanocrystal probe capable of bonding with a first detectable substance, if present, in said material, and capable of absorbing energy when exposed to said energy, said organo luminescent semiconductor nanocrystal probe comprising:
      i) a semiconductor nanocrystal capable of absorbing energy over a broad bandwidth when exposed to said energy;
      ii) an affinity molecule capable of selectively bonding to said detectable substance; and
      iii) a linking agent linked to said first semiconductor nanocrystal and also linked to said affinity molecule;
   b) removing, from said material, portions of said organo luminescent semiconductor nanocrystal probe not bonded to said first detectable substance; and
   c) exposing said material to energy capable of being absorbed by said first semiconductor nanocrystal, indicative of the presence of said first detectable substance in said material; and
   d) detecting the change in absorbed energy, indicative of the presence of said organo luminescent semiconductor nanocrystal probe in said material bonded to said detectable substance.

29. The process of claim 28 wherein at least one further organo luminescent semiconductor nanocrystal probe is used to treat said material, with each of said organo luminescent semiconductor nanocrystal probes selectively bondable to a different detectable substance and each of said organo luminescent semiconductor nanocrystal probes capable of absorbing energy over a broad bandwidth, whereby a plurality of detectable substances may be simultaneously analyzed for in a material using a single excitation source.

30. The process for treating a material of claim 28 wherein said step of exposing said material to energy capable of exciting said first semiconductor nanocrystal to absorb energy further comprises exposing said material to a source of electromagnetic radiation capable of emitting photons of a broad or narrow spectrum.

31. The process for treating a material of claim 28 wherein said step of exposing said material to energy capable of exciting said first semiconductor nanocrystal to absorb energy further comprises exposing said material to an X-ray source.

32. A process for treating a material to determine the presence of a detectable substance in said material which comprises:
   a) contacting said material with an organo luminescent semiconductor nanocrystal probe capable of bonding with a first detectable substance, if present, in said material, and capable of scattering or diffracting energy when excited, said organo luminescent semiconductor nanocrystal probe comprising:
      i) a semiconductor nanocrystal capable of scattering or diffracting energy over a broad bandwidth with a characteristic cross-section;
      ii) an affinity molecule capable of selectively bonding to said detectable substance; and
      iii) a linking agent linked to said first semiconductor nanocrystal and also linked to said affinity molecule;
   b) removing, from said material, portions of said organo luminescent semiconductor nanocrystal probe not bonded to said first detectable substance; and
   c) exposing said material to energy capable of exciting said first semiconductor nanocrystal to scatter or diffract energy, indicative of the presence of said first detectable substance in said material; and
   d) detecting the change in scattered or diffracted energy, indicative of the presence of said organo luminescent semiconductor nanocrystal probe in said material bonded to said detectable substance.

33. The process of claim 32 which includes the further step of treating said material with at least a second organo luminescent semiconductor nanocrystal probe capable of bonding to a second detectable substance in said material, and containing a second semiconductor nanocrystal also capable of scattering or diffracting energy, resulting in a detectable change in scattering cross-section, and whereby the exposure of said material to energy capable of scattering or diffracting from both said first and second nanocrystals will cause any of said first or second semiconductor nanocrystals present in said material to scatter or diffract energy with scattering cross sections characteristic of the particular organo luminescent semiconductor nanocrystal probe, whereby the presence or absence of more than one detectable substance in a material may be simultaneously detected using a single excitation energy source.

34. The process of claim 33 wherein at least one further organo luminescent semiconductor nanocrystal probe is used to treat said material, with each of said organo luminescent semiconductor nanocrystal probes selectively bondable to a different detectable substance and each of said organo luminescent semiconductor nanocrystal probes exhibiting a different scattering cross section and capable of scattering or diffracting energy, whereby a plurality of detectable substances may be simultaneously analyzed for in a material using a single excitation source.

35. The process for treating a material of claim 32 wherein said step of exposing said material to energy capable of exciting said first semiconductor nanocrystal to scatter or diffract energy further comprises exposing said material to an electron beam or other particle beam.

36. The process for treating a material of claim 32 wherein said step of exposing said material to energy capable of exciting said first semiconductor nanocrystal to scatter or diffract energy further comprises exposing said material to an X-ray source.

37. The process for treating a material of claim 32 wherein said step of exposing said material to energy capable of causing said first semiconductor nanocrystal to scatter or diffract energy, and said step of detecting said scattering or diffraction of energy, are both carried out using a transmission electron microscope.

38. The process for treating a material of claim 32 wherein said step of exposing said material to energy capable of causing said first semiconductor nanocrystal to scatter or diffract energy, and said step of detecting said scattering or diffraction of energy, are both carried out using a scanning electron microscope.

39. A luminescent semiconductor nanocrystal compound capable of linking to an affinity molecule and capable of absorbing energy in a narrow wavelength band comprising:
   a) a semiconductor nanocrystal capable of absorbing energy in a narrow wavelength band; and
   b) at least one linking agent linked to said semiconductor nanocrystal and capable of linking to said affinity molecule.

40. A luminescent semiconductor nanocrystal compound capable of linking to an affinity molecule and capable of scattering or diffracting energy in a narrow wavelength band when excited comprising:
   a) a semiconductor nanocrystal capable of scattering or diffracting energy in a narrow wavelength band when excited; and
   b) at least one linking agent linked to said semiconductor nanocrystal and capable of linking to said affinity molecule.

41. An organo luminescent semiconductor nanocrystal probe capable of bonding with a detectable substance and capable of absorbing energy in a narrow wavelength band, comprising a luminescent semiconductor nanocrystal compound linked to an affinity molecule capable of bonding to said detectable substance.

42. An organo luminescent semiconductor nanocrystal probe capable of bonding with a detectable substance and capable of absorbing energy in a narrow wavelength band comprising:
   a) a semiconductor nanocrystal capable of absorbing energy in a narrow wavelength band;
   b) at least one linking agent linked to said semiconductor nanocrystal and having a second portion capable of lining to an affinity molecule; and
   c) an affinity molecule linked to said second portion of said linking agent, and capable of selectively bonding to said detectable substance;
whereby treatment of a material with said organo luminescent semiconductor nanocrystal probe, and subsequent exposure of said treated material to energy to determine the presence of said detectable substance within said material will cause said semiconductor nanocrystal in said organo luminescent semiconductor nanocrystal probe, bonded to said detectable substance, to absorb energy of a narrow wavelength band signifying the presence, in said material, of said detectable substance bonded to said organo luminescent semiconductor nanocrystal probe.

43. An organo luminescent semiconductor nanocrystal probe capable of bonding with a detectable substance and capable of scattering or diffracting energy in a narrow wavelength band when excited, comprising a luminescent semiconductor nanocrystal compound linked to an affinity molecule capable of bonding to said detectable substance.

44. An organo luminescent semiconductor nanocrystal probe capable of bonding with a detectable substance and capable of scattering or diffracting energy in a narrow wavelength band when excited comprising:
   a) a semiconductor nanocrystal capable of scattering or diffracting energy in a narrow wavelength band when excited;
   b) at least one linking agent linked to said semiconductor nanocrystal and having a second portion capable of linking to an affinity molecule; and
   c) an affinity molecule linked to said second portion of said linking agent, and capable of selectively bonding to said detectable substance;

whereby treatment of a material with said organo luminescent semiconductor nanocrystal probe, and subsequent exposure of said treated material to excitation energy to determine the presence of said detectable substance within said material will excite said semiconductor nanocrystal in said organo luminescent semiconductor nanocrystal probe bonded to said detectable substance causing the scattering or diffracting of energy of a narrow wavelength band signifying the presence, in said material, of said detectable substance bonded to said organo luminescent semiconductor nanocrystal probe.

45. A process for forming a luminescent semiconductor nanocrystal compound capable of linking to an affinity molecule and capable of absorbing energy in a narrow wavelength band when excited which comprises: linking together a semiconductor nanocrystal capable of absorbing energy in a narrow wavelength band and a linking agent having a first portion linked to said semiconductor nanocrystal and a second portion capable of linking to an affinity molecule.

46. A process for forming a luminescent semiconductor nanocrystal compound capable of linking to an affinity molecule and capable of scattering or diffracting energy in a narrow wavelength band when excited which comprises: linking together a semiconductor nanocrystal capable of scattering or diffracting energy in a narrow wavelength band when excited and a linking agent having a first portion linked to said semiconductor nanocrystal and a second portion capable of linking to an affinity molecule.

47. A process for forming an organo luminescent semiconductor nanocrystal probe capable of bonding with a detectable substance and capable of absorbing energy in a narrow wavelength band which comprises linking a luminescent semiconductor nanocrystal compound with an affinity molecule capable of bonding with a detectable substance.

48. A process for forming an organo luminescent semiconductor nanocrystal probe capable of bonding with a detectable substance and capable of absorbing energy in a narrow wavelength band which comprises the steps of:
   a) linking a semiconductor nanocrystal capable of absorbing energy in a narrow wavelength band with a liing agent having a first portion linked to said semiconductor nanocrystal and a second portion capable of linking to an affinity molecule; and
   b) linking said linking agent and an affinity molecule capable of bonding with said detectable substance.

49. A process for forming an organo luminescent semiconductor nanocrystal probe capable of bonding with a detectable substance and capable of scatterin or diffracting energy in a narrow wavelength band when excited which comprises linking a luminescent semiconductor nanocrystal compound with an affinity molecule capable of bonding with a detectable substance.

50. A process for forming an organo luminescent semiconductor nanocrystal probe capable of bonding with a detectable substance and capable of scattering or diffracting energy in a narrow wavelength band when excited which comprises the steps of:
   a) linking a semiconductor nanocrystal capable of scattering or diffracting energy in a narrow wavelength band when excited with a linking agent having a first portion linked to said semiconductor nanocrystal and a second portion capable of linking to an affinity molecule; and
   b) linking said linking agent and an affinity molecule capable of bonding with said detectable substance.

* * * * *

UNITED STATES PATENT AND TRADEMARK OFFICE
CERTIFICATE OF CORRECTION

PATENT NO.    : 5,990,479                                    Page 1 of 1
DATED         : November 23, 1999
INVENTOR(S)   : Weiss et al.

It is certified that error appears in the above-identified patent and that said Letters Patent is hereby corrected as shown below:

<u>Column 6,</u>
Line 7, change "5,251,018" to -- 5,751,018 --.

Signed and Sealed this

Twenty-sixth Day of February, 2002

Attest:

JAMES E. ROGAN
Attesting Officer    Director of the United States Patent and Trademark Office